United States Patent [19]

Pogany et al.

[11] Patent Number: 5,254,345
[45] Date of Patent: Oct. 19, 1993

[54] POLY(ORTHOCARBONATE ACETAL) BIOERODIBLE POLYMERS

[75] Inventors: Stefano A. Pogany; Gaylen M. Zentner, both of Lawrence, Kans.

[73] Assignee: Merck & Co., Inc., Rahway, N.J.

[21] Appl. No.: 774,667

[22] Filed: Oct. 11, 1991

[51] Int. Cl.⁵ .................. A61F 2/02; A01N 25/08; A61K 9/14; A61K 31/765
[52] U.S. Cl. .................. 424/426; 424/409; 424/484; 424/486; 514/772.5; 528/205; 528/219; 528/392; 528/406
[58] Field of Search ............... 424/409, 426, 484, 486, 424/78.08, 78.38; 514/772.5; 528/205, 219, 392, 406

[56] References Cited

U.S. PATENT DOCUMENTS

| | | |
|---|---|---|
| 4,093,709 | 6/1978 | Choi et al. ............... 424/424 |
| 4,304,767 | 12/1981 | Heller et al. ............... 424/428 |
| 5,013,821 | 5/1991 | Heller et al. ............... 424/428 |

FOREIGN PATENT DOCUMENTS 0168277 1/1986 European Pat. Off. .
0419156 3/1991 European Pat. Off. .

OTHER PUBLICATIONS

H. Tagoshi and T. Endo, *The Chemical Society of Japan, Chemistry Letters*, pp. 2363-2364, 1987.

*Primary Examiner*—Thurman K. Page
*Assistant Examiner*—Carlos Azpuru
*Attorney, Agent, or Firm*—Francis P. Bigley; Mark R. Daniel; Joseph F. DiPrima

[57] ABSTRACT

Polymers obtained by condensing polyols with divinyl orthocarbonates are useful for making bioerodible polymers for sustained release of beneficial agents.

7 Claims, No Drawings

POLY(ORTHOCARBONATE ACETAL) BIOERODIBLE POLYMERS

BACKGROUND OF THE INVENTION

U.S. Pat. No. 4,093,709 describes biodegradable (or "bioerodible") ortho ester polymers. The polymers are the reaction products of an orthoester or orthocarbonate with a polyol. The reaction is carried out at elevated temperature, under reduced pressures and requires a relatively long reaction time. A drug or other beneficial agent is entrapped (dispersed) in the polymer and is released therefrom by diffusion or a combination of diffusion and polymer degradation.

U.S. Pat. No. 4,304,767 describes poly(orthoester) polymers that are made by reacting a ketene acetal having a functionality of two or more with hydroxyl containing compounds having a functionality of two or more.

OBJECTS OF THE INVENTION

It is an object of the present invention to provide new bioerodible polymers by condensing a polyol with a divinyl orthocarbonate to form a poly(orthocarbonate acetal). Another object is to provide new bioerodible polymers having an acid labile moiety comprising an orthocarbonate and an acetal group that share in common an oxygen atom. A further object is to provide a method for preparing these bioerodible polymers. These and other objects of the present invention will be apparent from the following description.

SUMMARY OF THE INVENTION

Bioerodible polymers are obtained by reacting a polyol with a divinyl orthocarbonate under condensing conditions in the absence of a radical initiator. The resulting polymer comprises an acid labile moiety having an orthocarbonate and an acetal group sharing in common an oxygen atom.

DETAILED DESCRIPTION

The present invention relates to bioerodible polymers that are prepared by condensing a polyol with a divinyl orthocarbonate. Due to their bioerodible nature the polymers of the present invention are useful in the preparation of devices and coatings for delivering beneficial agents to an environment of use. Exemplary environments of use include, without limitation thereto, oral, gastrointestinal, rectal, vaginal, ocular, and nasal cavities of humans and animals. Other environments of use include parenteral sites of administration to humans and animals. Agricultural applications where the environment of use is the cultivation site are included.

The term "beneficial agent" means a compound or composition that provides a desired and useful effect upon the environment or individual (man or animal) to which it is administered. This term includes, without limitation, such agents as drugs, pharmaceuticals, biologicals, nutrients, plant growth regulants, pesticides, catalysts, disinfectants, and the like. Specific examples of beneficial agents may be found in, for instance, *The Merck Index*, 11th ed., Merck & Co., Inc.

The term "effective amount" means at least that quantity of beneficial agent that is required to provide the intended or desired effect and wherein any side effects are within acceptable limits.

The polyol reactant can be described as comprising diols and crosslinking agents:

1. Diols with the structure HO—R—OH wherein R is
   a) a linear hydrocarbon chain with a total carbon number of from 2 to about 20, specific examples of which are 1,4-butanediol, 1,5-pentanediol, 1,6-hexanediol, 1,7-heptanediol, 1,8-octanediol, 1,9-nonanediol, 1,10-decanediol, and the like;
   b) a branched hydrocarbon chain with a total carbon number between 4 and about 20, specific examples of which are 3,3-dimethylpentanediol, 2,3-dimethyl-1,6-hexanediol, 3,6-diethyl-1,9-nonanediol, and the like;
   c) a cyclic hydrocarbon with a total carbon number between 3 and about 20, specific examples of which are cyclohexanedimethanol, 1,4-benzenedimethanol, and the like,
   d) a hydrocarbon residue containing one or more heteroatoms such as oxygen, nitrogen or sulfur in the main chain, or one or more heteroatoms such as oxygen, nitrogen, halide (F, Cl, Br or I) or sulfur in a side group, specific examples of which are triethylene glycol, tetraethylene glycol, n-butyldiethanolamine, polyethylene glycols, and the like;
   e) any diol from groups a) through d) above wherein at least one carbon atom in —R— is replaced by silicon;
   f) a combination of diols from at least two of groups a) through e);

2. Crosslinking agents with the structure $R(OH)_m$ wherein R has the same meaning as R in definition 1 above and m is $\geq 3$. Specific examples of such crosslinking agents are 1,2,6-hexanetriol, tromethamine, glycerol, pentaerythritol, 2-ethyl-2-hydroxymethyl-1,3-propanediol, glucose, and 1,3,5-cyclohexanetriol.

In addition, compounds having two or more phenolic hydroxyl groups or compounds having at least one phenolic group and at least one hydroxyl group may also be employed as the polyol reactant. Examples of such compounds are hydroquinone, catechol, resorcinol, 4,4'-isopropylidenediphenol, pyrogallol, hydroxyhydroquinone, phloroglucinol and propyl gallate and 4-hydroxybenzyl alcohol. Beneficial agents containing two or more hydroxyl groups also can serve, in whole or part, as the polyol reactant.

Oxides and hydroxides such as, for example, MgO, $Mg(OH)_2$, CaO, $Ca(OH)_2$, carbonates and bicarbonates such as, for example, $MgCO_3$, $Na_2CO_3$ and $NaHCO_3$, and organic amines such as, for example, tromethamine and triethylamine act to stabilize the polymer bonds and slow the hydrolytic breakdown.

The divinyl orthocarbonate is a tetraoxaspiro compound. Specific examples of such divinyl orthocarbonates are, for instance, 2,7-dimethylene-1,4,6,9-tetraoxaspiro[4.4]nonane and 3,9-dimethyl-1,5,7,11-tetraoxaspiro[5.5]undeca-2,8-diene. These divinyl orthocarbonates can be represented by the formulas

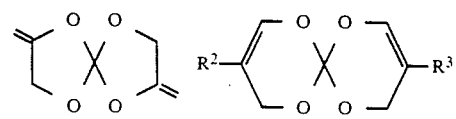

wherein $R^2$ and $R^3$ are independently H or a linear or branched hydrocarbon moiety of from 1 to about 10 carbon atoms.

The reaction between the polyol and the divinyl orthocarbonate takes place under condensing conditions in the absence of a radical initiator. The reaction can be carried out neat (absence of solvent) or in an aprotic solvent such as, for example, tetrahydrofuran (THF), glyme (ethylene glycol dimethyl ether), diglyme, cymene, cumene, p-dioxane or chlorinated hydrocarbons. In all cases anhydrous conditions should be maintained. The reaction preferably is effected at temperatures of from about 30° C. to about 150° C. for from about 1 hour to about 24 hours. The approximate mole ratio of reactants (divinyl ether:diol) is from about 3:2 to about 2:3, preferably about 1:1. While these ratios may be varied somewhat, extensive variation is not preferred as the molecular weight range of the bioerodible polymer product is dependent upon the mole ratio of the reactants. The highest molecular weights are obtained when the mole ratio is 1:1 and decreases when either reactant is present in excess. The condensation reaction proceeds according to the following example reactions:

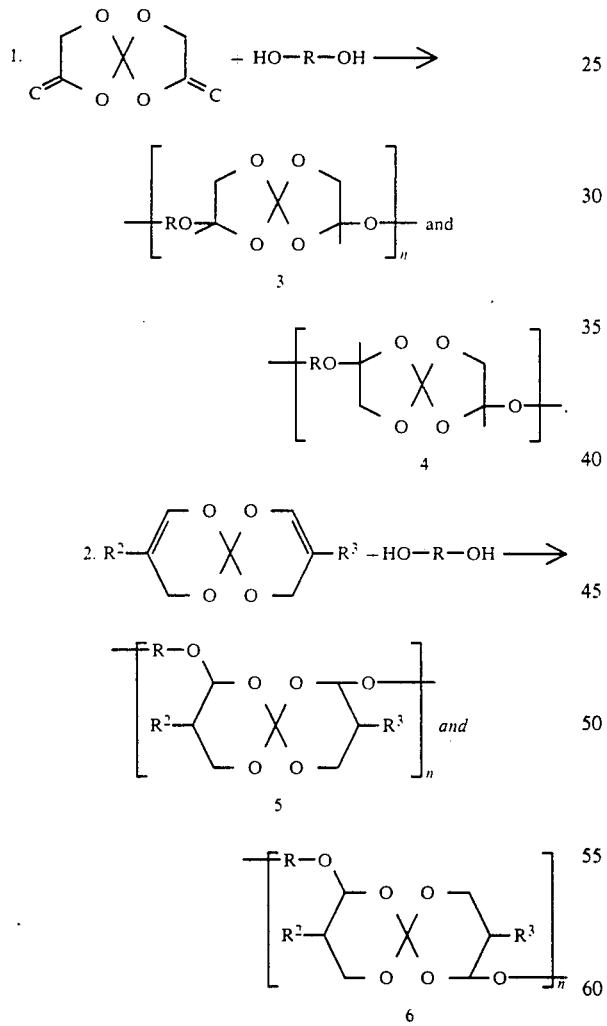

wherein n is an integer of from about 5 to about 1,000, preferably from about 5 to about 500, and most preferably from about 10 to about 500.

The beneficial agent can be incorporated into the polymer by being physically admixed with the polymer or by being covalently bound to the polymer. When the beneficial agent has two or more hydroxyl groups, it can be incorporated into the polymer in the same manner as the diol or polyol reactant.

The beneficial agent can be incorporated into the polymer by various mixing techniques that will be selected based upon the properties of the beneficial agent and the polymer. If the beneficial agent contains at least two hydroxy groups, it can be covalently bonded to and become part of the polymer itself.

The following examples illustrate the present invention without, however, limiting the same thereto.

EXAMPLE 1

10 grams (0.0640 moles) of 2,7-dimethylene-1,4,6,9-tetraoxaspiro[4.4]nonane and 7.54 grams (0.0640 moles) of 1,6-hexanediol are weighed into a 200 mL 3-necked, paddle stirred flask under rigorously anhydrous conditions. The anhydrous conditions are maintained while 50 mL of dried tetrahydrofuran is added to the flask and the stirrer activated. The reaction flask is thermostatted at 50° C. After stirring for about one hour the poly(orthocarbonate acetal) is isolated by either precipitation into a hydrocarbon solvent which contains a small amount of triethylamine followed by filtration, or by evaporation of the solvent in a Teflon coated pan in-vacuo.

The polymer has the structure shown in formulas 3 and 4 wherein R is $-H_2C(CH_2)_4CH_2-$.

EXAMPLE 2

Following the procedure of Example 1, but replacing 1,6-hexanediol with either trans-1,4-cyclohexane dimethanol, 1,2-propanediol, tetraethylene glycol, triethylene glycol, 2-methyl-1,3-propanediol and 1,7-heptanediol, the corresponding polymers of formulas 3 and 4 are formed wherein R is

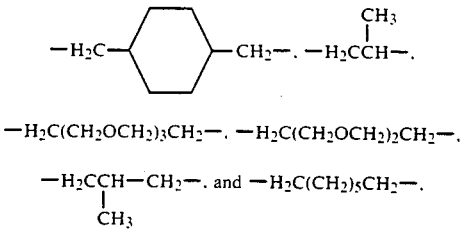

$-H_2C(CH_2OCH_2)_3CH_2-$, $-H_2C(CH_2OCH_2)_2CH_2-$, $-H_2CCH(CH_3)-CH_2-$, and $-H_2C(CH_2)_5CH_2-$.

respectively.

EXAMPLE 3

Following the procedure of Example 1, 10 grams (0.0543 moles) of 3,9-dimethyl-1,5,7,11-tetraoxaspiro[5.5]undeca-2,8-diene and 6.41 grams (0.0543 moles) of 1,6-hexanediol are reacted in 100 mL of anhydrous tetrahydrofuran to produce the polymer whose structure is shown in formulas 5 and 6 wherein $R^2$ and $R^3$ are each methyl and R is $-H_2C(CH_2)_4CH_2-$.

EXAMPLE 4

Following the procedure of Example 3, but replacing 1,6-hexanediol with either trans-1,4-cyclohexane dimethanol, 1,2-propanediol, tetraethylene glycol, triethylene glycol, 2-methyl-1,3-propanediol and 1,7-heptanediol, the corresponding polymers of formulas 5 and 6 are formed wherein $R^3$ and $R^4$ are each methyl and R is

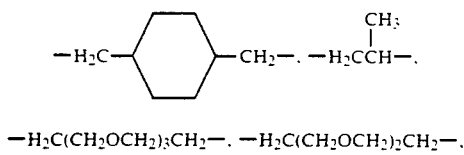

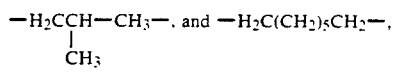

EXAMPLE 5

Following the procedures in Examples 1 and 3, but replacing 1,6-hexanediol with 0.043 moles or 0.036 moles of 1,2,6-hexanetriol respectively, the corresponding crosslinked polymers are obtained.

EXAMPLE 6

Drug delivery devices are prepared by dissolving 10 grams of the linear polymer of Example 1 in 50 mL of tetrahydrofuran, adding 0.5 grams of magnesium oxide as a stabilizer, and 2 grams of ivermectin as beneficial agent and removing the solvent. Sheets of the polymer mixture are produced and $\frac{1}{4}''$ (0.63 cm) discs are punched from these sheets. These discs are suitable for controlled sustained delivery of the ivermectin to an environment of use such as the gastrointestinal tract or subcutaneous implant site.

EXAMPLE 7

An Atlantic Research 2CV Helicone Mixer is heated to 60° C. in a low humidity room (approximately 70° F. and 5% RH). Tetraethylene glycol (5.5702 gm), 1,6-hexanediol (3.3899 gm), 1,2,6-hexanetriol (2.0437 gm), magnesium oxide (0.8957 gm) and ivermectin (7.1997 gm) pre-dried in-vacuo to reduce residual solvents, are added to the mixer and stirred for 1 minute. 2,7-dimethylene-1,4,6,9-tetraoxaspiro-[4.4]nonane (ratio of vinyl ether groups: hydroxyl groups from polyols (excluding ivermectin) is 0.98) is added as a liquid to the mixture and is stirred at a moderate speed (setting "6") until a viscosity of approximately 16,600 cp (20° C.; 10 sec$^{-1}$) is achieved. The mixture is then dispensed into FEP teflon tubing and cured at 60° C. The poly(orthocarbonate acetal) rods are removed from the tubing after cooling to room temperature. The implants contain 20 wt % total ivermectin, with 20 to 60% of the ivermectin incorporated into the polymer matrix via covalent bonds.

What is claimed is:

1. A polymer having a plurality of acid labile groups comprising an orthocarbonate and an acetal group sharing in common an oxygen atom, the polymer having from about 5 to about 1000 units, the units selected from the group consisting of

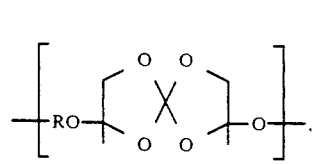

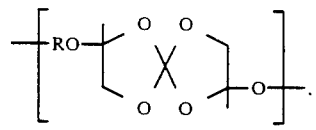

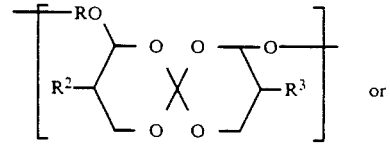

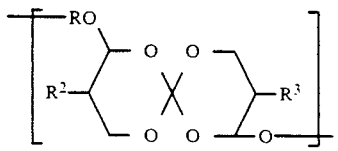

wherein R is
- (a) a linear hydrocarbon chain with a total of from 2 to about 20 carbon atoms,
- (b) a branched hydrocarbon chain with a total of from 4 to about 20 carbon atoms,
- (c) a cyclic hydrocarbon with a total of from 3 to about 20 carbon atoms,
- (d) a hydrocarbon residue containing in the main chain or, if branched, in either the main chain or the branched chain at least one heteroatom, selected from the group consisting of O, N, S or halogen,
- (e) any hydrocarbon defined in (a), (b), (c) or (d) wherein at least one carbon atom is replaced by silicon, and $R^2$ and $R^3$ are independently H or a linear or branched hydrocarbon moiety of from 1 to about 10 carbon atoms.

2. A polymer according to claim 1 wherein the number of units is from about 5 to about 500.

3. A polymer according to claim 1 wherein the number of units is from about 10 to about 500.

4. A polymer of the formula $(Z)_n$ wherein Z is at least one unit selected from the units of claim 1 and n is an integer from about 10 to about 500.

5. A polymer according to claim 4 wherein Z comprises at least two different units.

6. A composition comprising a polymer according to claim 1 and a beneficial agent.

7. A polymer according to claim 1 formed by condensing a polyol and a divinyl orthocarbonate in the absence of a radical initiator.

* * * * *